US008639529B2

(12) United States Patent
Lee

(10) Patent No.: US 8,639,529 B2
(45) Date of Patent: Jan. 28, 2014

(54) METHOD AND DEVICE FOR MAINTAINING AND PROVIDING ACCESS TO ELECTRONIC CLINICAL RECORDS

(75) Inventor: Keat Jin Lee, Guilford, CT (US)

(73) Assignee: E-Web, LLC, Guilford, CT (US)

( * ) Notice: Subject to any disclaimer, the term of this patent is extended or adjusted under 35 U.S.C. 154(b) by 247 days.

(21) Appl. No.: 11/640,167

(22) Filed: Dec. 15, 2006

(65) Prior Publication Data
US 2007/0124178 A1 May 31, 2007

Related U.S. Application Data

(63) Continuation-in-part of application No. 11/343,383, filed on Jan. 30, 2006.

(60) Provisional application No. 60/695,646, filed on Jun. 29, 2005.

(51) Int. Cl.
*G06Q 50/00* (2012.01)
*G06Q 40/00* (2012.01)

(52) U.S. Cl.
USPC .................................. 705/3; 705/4; 705/328

(58) Field of Classification Search
USPC .......................................................... 705/2, 3
See application file for complete search history.

(56) References Cited

U.S. PATENT DOCUMENTS 6,546,230 B1 * 4/2003 Allison .......................... 434/350
6,801,227 B2 * 10/2004 Bocionek et al. ............. 715/777
6,997,717 B2 * 2/2006 Kienzle et al. ................ 434/262
2002/0029223 A1 * 3/2002 Rice et al. ................... 707/104.1
2002/0032582 A1 * 3/2002 Feeney et al. ..................... 705/2
2002/0035484 A1 * 3/2002 McCormick ....................... 705/2
2002/0045154 A1 * 4/2002 Wood et al. .................... 434/350
2003/0028399 A1 * 2/2003 Davis et al. ....................... 705/2
2003/0061096 A1 * 3/2003 Gallivan et al. ................. 705/14
2003/0113370 A1 * 6/2003 Firestone et al. ............. 424/452
2003/0236683 A1 12/2003 Henderson et al.
2004/0107118 A1 6/2004 Harnsberger et al.
2004/0111622 A1 * 6/2004 Schoenberg ................... 713/182
2009/0076857 A1 * 3/2009 Eletreby et al. ................... 705/3
2009/0254378 A1 * 10/2009 Janas et al. ......................... 705/3
2010/0223672 A1 * 9/2010 Maher et al. ................... 726/26

FOREIGN PATENT DOCUMENTS

WO WO 9624213 A1 * 8/1996

OTHER PUBLICATIONS

Pray, Walter Steven, Ph.D, "The Development of a Standardized Competency Examination for Doctor of Pharmacy Students," 1983, Purdue University, (abstract).*

(Continued)

*Primary Examiner* — Rachel L Porter
(74) *Attorney, Agent, or Firm* — MKG, LLC

(57) ABSTRACT

In a method for accessing, recording and maintaining the clinical records of medical patients, a database is established for receiving and maintaining comprehensive clinical records of medical patients. The database is remotely accessible by one or more care givers and has software-based programming associated therewith. The database us populated with patients' clinical records and is remotely accessible to electronically retrieve at least a portion of the patient's clinical records. The clinical records are downloaded and displayed for viewing by the caregiver. Advertisements can also be displayed for viewing by the caregiver upon accessing the database.

7 Claims, 14 Drawing Sheets

(56) References Cited

OTHER PUBLICATIONS

Webster, Brian, "KNOWing What They Know," May 2006. Pharmaceutical Executive. p. 8.*

LoBouno, Charlotte; "Task force issues report on safe sedation practices," Sep. 18, 2006; Drug Topics; 2 pages.*

Schwertz D W; Piano M R; Kleinpell R; Johnson J; "Teaching pharmacology to advanced practice nursing students: issues and strategies." Feb. 1997, vol. 8 No. 1, pp. 132-146.*

Office Action dated Aug. 17, 2009.

\* cited by examiner

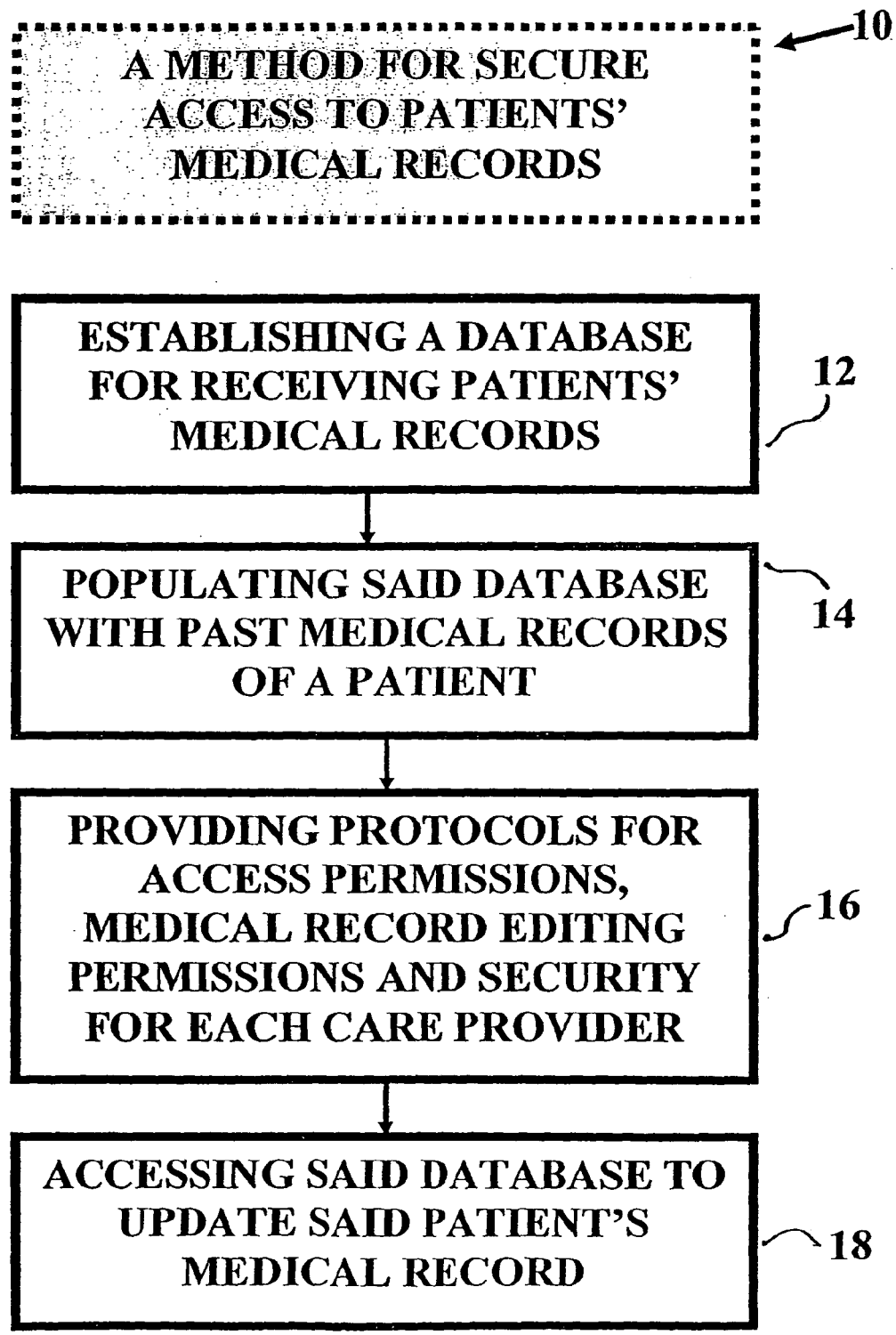

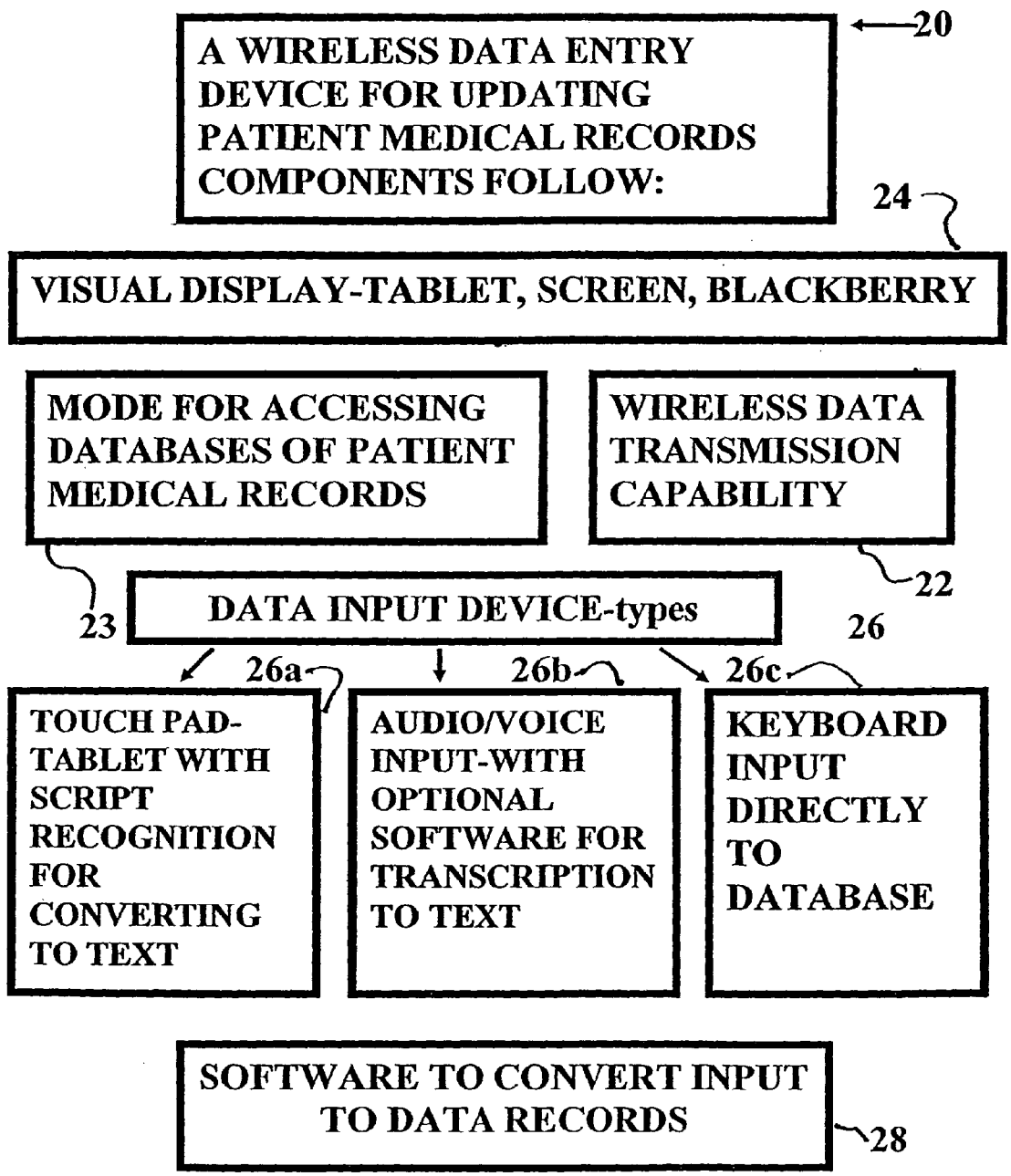

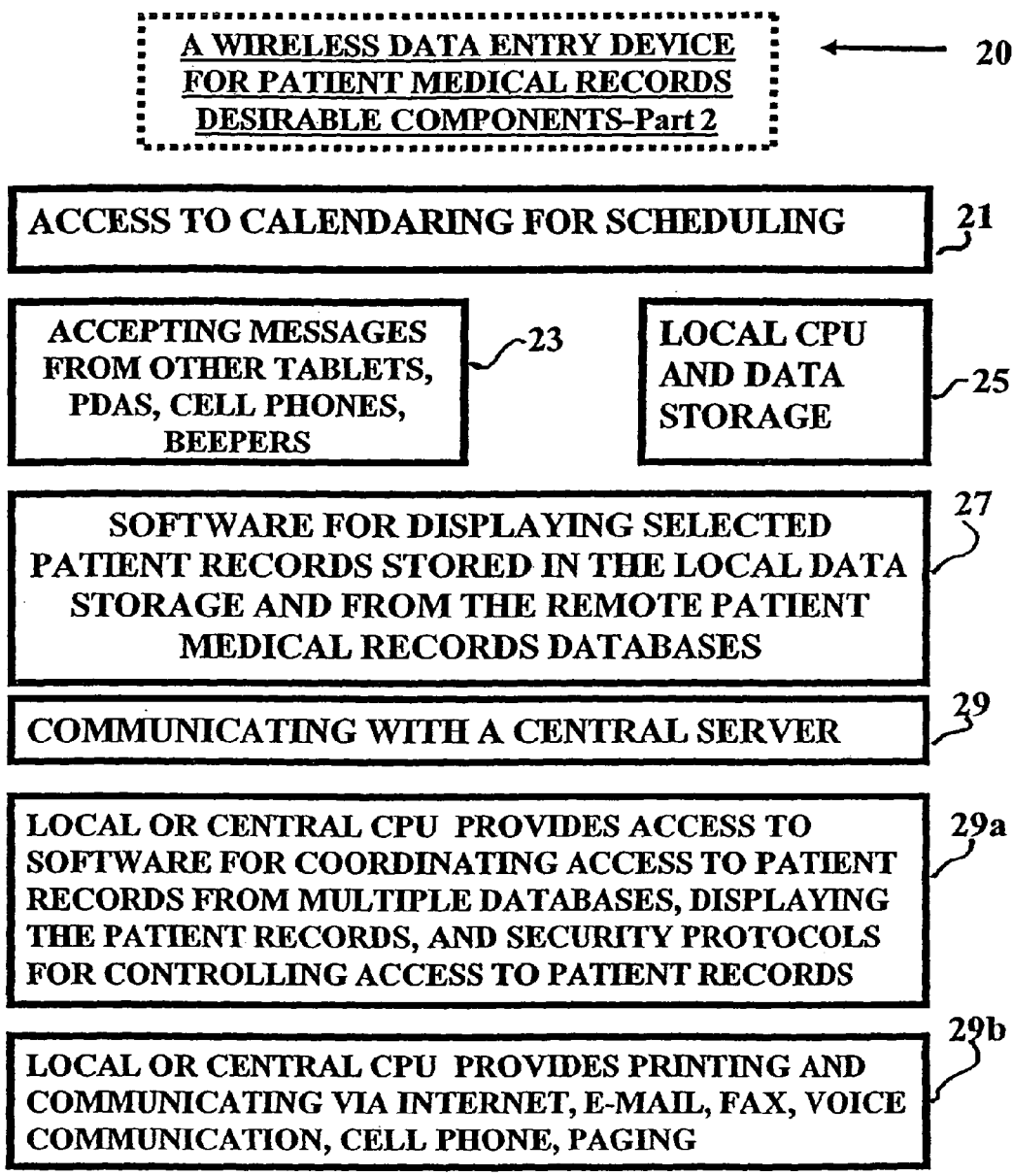

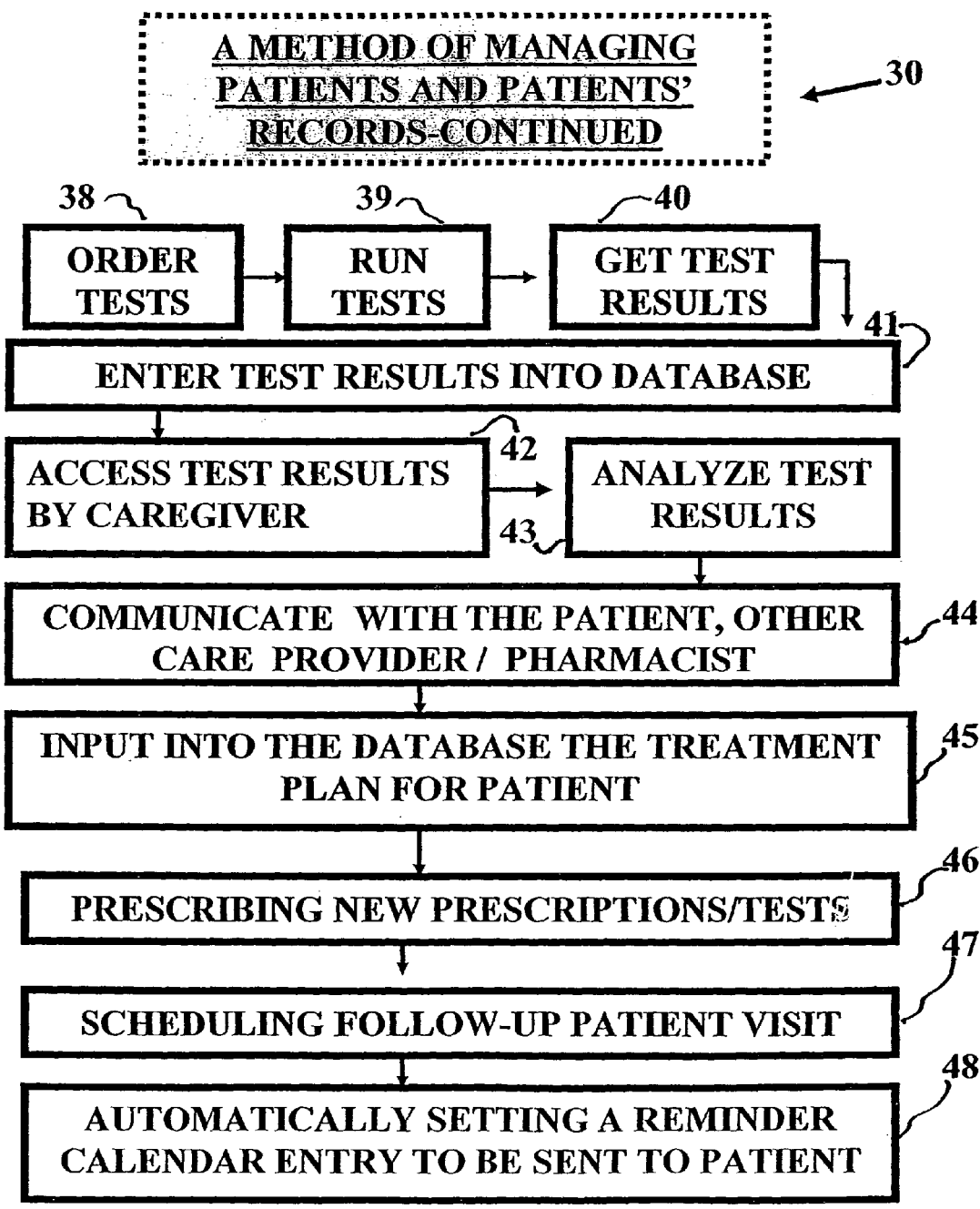

METHOD AND DEVICE FOR MAINTAINING AND PROVIDING ACCESS TO ELECTRONIC CLINICAL RECORDS

CROSS REFERENCE TO RELATED APPLICATIONS

This patent application is a continuation in part of U.S. patent application Ser. No. 11/343,383, filed Jan. 30, 2006, which claims the benefit under 35 U.S.C. Section 119(e) of U.S. Provisional Patent Application Ser. No. 60/695,646, filed Jun. 29, 2005, the disclosures of which are incorporated by reference herein in their entirety.

FIELD OF THE INVENTION

The present invention relates generally to patient clinical records and is more specifically directed to efficient methods of accessing, safeguarding and utilizing such records electronically.

BACKGROUND OF THE INVENTION

Normally, when a patient sees a doctor or other care provider, the patient is put into an examination room. The care provider then retrieves the patient's "paper file" which may contain test results and a medical history. Generally, this "paper" medical history deals only with the interactions between the particular care provider and the patient and does not include or includes only minimal information regarding any interactions between the patient and different care providers. This lack of medical information can put a care provider to a great disadvantage as the patient may not be forthcoming enough to appropriately inform the care provider of such things as medications being taken, or other ailments that may impact healthcare decisions the care provider needs to make. As a result, medical errors may be made or expensive tests may be duplicated unnecessarily.

Another difficulty occurs where a patient may have a procedure scheduled in a hospital. The procedure may entail consultations with several medical personnel specializing in different disciplines. Typically these medical personnel will need to review the patient's medical history and clinical records. These records would include the results of any tests the patient may have undergone. This in all likelihood will involve interfacing with other care providers and testing facilities to have the clinical records forwarded to the care providers having a need to review them. It is often difficult to coordinate the timely collection of these records and the potential for human error is significant. In addition, even if the clinical records are supplied on a timely basis, different care providers within the hospital must forward the records to other care providers that need to view them. This further adds to the potential for human error.

Based on the foregoing, it is the general object of the present invention to improve upon or overcome the problems associated with the prior art.

SUMMARY OF THE INVENTION

As used herein, the term "care provider" should be broadly construed to include, but not be limited to, doctors, nurses, physician's assistants, emergency medical technicians, paramedics, nursing home workers, diagnostic laboratories and medical testing facilities authorized to access the clinical records.

The present invention is directed in one aspect to a method of efficiently recording a patient's clinical record and in another aspect to a method that allows for secure access to patients' clinical records by authorized personnel and by the patients also efficiently. At all junctures, the patients have control over their records for privacy purposes. Normally, when a patient sees a doctor or other care provider, the patient is put into an examination room. The care provider then retrieves the patient's "paper file" which may contain test results and a medical history. Generally, this "paper" medical history deals only with the interactions between the particular care provider and the patient and does not include or includes only minimal information regarding any interactions between the patient and different care providers. This can put a care provider to a great disadvantage as the patient may not be forthcoming enough to appropriately inform the care provider of medications being taken, or other ailments that may impact healthcare decisions the care provider needs to make. As a result, medical errors may be made or expensive tests may be duplicated unnecessarily. This invention has the capability of arranging the electronic clinical records to just open up a particular provider's file for a patient or to open the clinical records of other care providers who also cared for the patient. In order for one care provider to view the clinical records of other care providers, the permission of the patient is required.

In the method of the present invention, a database is established for containing patient clinical records. This database can be internal to a practice or facility or it can be accessible via the internet or other secure server by any number of care providers authorized by the patient to access the clinical records. Medical information is input into the database by authorized care providers or staff into the record of that particular care provider. While a care provider may have access to the database to input information regarding his/her care of the patient, the provider may not input into other provider's records. With the patient's approval, a care provider may view other care provider's records but cannot make any input into other care provider's records of the patient.

The present invention also contemplates the use of portable devices such as personal digital assistants, pocket personal computers, laptop computers and tablet-based devices that include touch screen technology. For the purposes of the present invention, these types of devices will be referred to collectively as "tablets." Preferably, these tablets are equipped with wireless technology so that they can be used to access information as well as input information without having to be directly connected via a hard wire to a server, modem, DSL line or other hard wired connection.

In a typical scenario, a care provider can access a list of all of his/her appointments for a desired time period on his/her tablet. When a patient enters a facility for treatment and, if the individual is a first-time patient or an update of the medical history is necessary, is given a medical history form to fill out. If the patient is computer literate, the patient can be provided with a tablet to input the required information or, if the database is accessible over the internet, prior to his/her appointment, the patient can input the required information from their home or office computer. The computerized form will be set up and segmented to be easily understood and user friendly to manipulate. If the patient is not computer literate, a staff member can input the information based on a paper form filled out by the patient.

At the very least, the information required from a patient will include demographic information, known allergies to medications, current medications being taken and major illnesses. This information will be stored in the database in a segmented format with allergies to medications and current medications forming one segment or category, major illnesses being another category, etc.

Once the patient information is input into the database, the patient is generally escorted or sent to an examination room. The examination room into which the patient has been sent is input into the database or into a program that, among other things, provides access to, and allows for data manipulation regarding the information contained within the database. Once the patient is in the examination room, the care provider is alerted via an indicator on his/her tablet. The indicator can be audible, visual (a flashing portion of the screen or a blinking light), or a combination of visual and audible signals. The care provider can then tap or "click" an icon on the screen of his/her tablet corresponding to the examination room in which the patient has been placed and the patient's name and the information corresponding to the patient's last encounter appear on the tablet screen. The care provider is able to scroll to previous encounter information or search history by date and type of each segmented file.

The other information that appears can be in the form of a series of drop-down menus or electronic filing cabinets corresponding to various segmented aspects of the patient's medical history, or the complete history of the patient can be displayed with the care provider being able to scroll down the history or to search using keywords or dates. As the patient's examination progresses, the care provider will input information via the tablet. This can be accomplished by either typing the information into the tablet or by writing on the surface of the tablet which is programmed with character recognition software to convert the handwritten notations into the equivalent of typed text. Where the information is handwritten, a copy of the actual handwritten notes along with a copy of the converted typed notes can be saved so that if errors in the converted notes occur, the handwritten notes can be referred to. In addition, when inputting information, the program can allow the care provider to access a list of common phrases or diagnoses or other templates that the care provider may wish to input. In addition, the tablets can include, or be provided with, a microphone and be programmed with voice recognition software. In this case, a care provider can dictate into the tablet which automatically converting it into a transcribed text as well as a recording of the dictation being stored in the database.

When a care provider wishes to input notations concerning a patient, he/she would preferably open an electronic filing cabinet by "tapping" or "clicking" an icon on the tablet screen corresponding to the desired filing cabinet. Once open, the doctor can search the contents of the particular electronic filing cabinet by keywords, date, or by scrolling. If the care provider wishes to add material to the contents of the electronic filing cabinet, the care provider can start typing or writing on a touch-screen and the program will automatically input the information following the last entry. The information can also be scanned in or be electronically entered. The care provider can have access to a number of different electronic filing cabinets. For example, there can be filing cabinets for pathology, X-rays, MRI's, CAT scans, blood tests, attorney's correspondence, workman's compensation, ultrasounds, and correspondence between doctors. However, this list should not be considered exhaustive as any number of different filing cabinets can be set up and accessed.

In addition, there will be electronic filing cabinets established for different medical specialties. When a specialty is accessed, a list of doctors or other care providers of the patient will appear on the tablet and be selectable by the care provider accessing the electronic filing cabinet. Within each specialty, once a particular care giver is chosen, the current provider, with the patient's permission, can access and view that record but not amend or add to the record. A provider can only add or amend his/her own record for the patient.

Returning to the above-described example, if during a patient visit, the care provider orders tests to be conducted on a patient, the care provider can attend to other patients in the above-described manner while the first patient is undergoing the tests. Once the tests are completed, the facility or entity conducting these tests accesses the database and inputs the test results. Upon return after having had the prescribed tests, the patient is placed in the same or a different examination room. The care provider is alerted via his/her tablet as described above and clicks or taps on the icon displayed on the tablet corresponding to the examination room that the patient is in and is once again presented with information corresponding to the particular patient in the chosen examination room. The care provider can access the test results and discuss them with the patient. Where a period of time is required to obtain the test results, the tablet can also be used to alert the care provider that the results have been input into the database. The care provider can then contact the patient via conventional methods, or he/she can use the tablet to e-mail, fax or call (if the tablet is so configured) the patient regarding the results of the test.

Upon completion of a patient's visit to a care provider's facility, the care provider can input, using the tablet, the results of the visit and the patient's treatment plan. The care provider, if so authorized, can also input any necessary prescriptions into the tablet. The prescription can be printed either remotely at a staff person's work station, at a printer in the particular examination room, or if the tablet is so equipped, via an integral printer forming part of the tablet. The prescription can also be faxed or e-mailed to an authorized pharmacy directly from the tablet. When a care giver accesses the electronic filing cabinet corresponding to writing the prescriptions, the particular patient's drug allergy and other medication information is also displayed. If a care giver attempts to prescribe a drug to which the patient is allergic, the tablet will alert the care giver and/or prevent the prescription from being printed. In addition, the program running on the tablet will cross-reference the prescribed medication with any medications currently being taken by the patient and will compare the combination of drugs with reference sources, such as, but not limited to, the Physicians Desk Reference for any possible problems that may arise due to the medicinal combination.

If at any time a care provider needs to convey information to another care provider or staff member, the tablet can be programmed to call the other person(s) on their cell phone and a message can be played upon answer. In addition, the tablet can send an instant message to the cell phone or can page the person(s) via their beeper. The tablet can also be configured to accept messages from other tablets, cell phones, beepers, and other communications devices. Moreover, the tablet can be configured to cause a message to be printed at a desired location, such as, for example, in a hospital a doctor can use his/her tablet to order a test and while the patient is going to the area where the test is to be performed, the physician's instructions can be printed there.

Upon completion of the patient's visit, the care giver or a staff person will input insurance codes corresponding to the actions taken with respect to the patient during the visit. The program running on the tablet will interface with appropriate reference sources to insure that the proper insurance codes have been associated with the visit. This will minimize and perhaps prevent over-coding or under-coding with respect to the particular visit. When a care provider inputs a CPT code associated with tests performed on the patient, a list of diagnoses corresponding to the particular CPT code chosen can appear and then the care provider can choose the appropriate diagnosis code. Once the appropriate CPT code corresponding to the correct diagnosis code entry is complete, the insurance company can be automatically billed and any patient co-payment can be indicated.

Any follow-up visits to the care provider's facility can be input via a tablet with e-mail or fax reminders being automatically sent or standard mail reminders automatically generated. This information is also available to the secretary who is checking the patient out.

In another aspect of the present invention, when a patient has a question for a care provider, or has an emergency, the patient, a staff person, or an answering service can send a message via e-mail or telephone to the care provider's tablet. An indicator on the tablet will alert the care provider regarding the fact that there is a patient message. Depending on whether the message concerns an emergency or not, the alert level can change and may consist of flashing lights of differing colors, an audible alert, a message on a particular section of the tablet screen, or any combination thereof. Using the tablet, an authorized care provider can access a patient's medical history from any location where wireless or other access to the database is available. There will be a message queue indicating the order in which the messages were received. Depending on the decided upon manner of response, the care provider can e-mail the patient, call the patient, or e-mail instructions to a staff person to call the patient. The care provider can also use the tablet to send a fax to the patient.

The above described embodiments of the present invention are all predicated on high levels of security with respect to anyone having access to a patient's clinical records. The present invention is completely HIPPA compliant. Absolutely no access to a patient's records of another care giver will be permitted without first obtaining a patient's permission. (A provider can always view his/her own record of the patient.) Such permission can be given in a conventional manner by providing the entity desiring access with written permission. However, permission may also be given by employing a fingerprint or retina print recognition system whereby a copy of a patient's thumbprint or other fingerprint or retina print is stored in the database either separately or along with the particular patient's demographic information. A fingerprint or retina print reader can be located in a care giver's facility and when a patient arrives, his/her fingerprint or retina print can be scanned by the fingerprint or retina reader and in this manner permission to access the patient's other care providers' clinical records granted. The patient can also be required to enter a password along with the fingerprint or retina print. Once the security protocols have been met, a series of icons or other indicia can appear. The icons represent various different segmented files of the medical record. The patient can then choose the icons corresponding to the records that he/she wishes to give the care giver access to.

The above-described fingerprint or retina print reader can also be incorporated into the care provider's personal tablet. The patient would then grant permission using the care-provider's tablet. In addition, the fingerprint or retina print reader can also be employed to prevent unauthorized use of a particular tablet. When such is the case, the care provider would have to swipe his/her finger over the fingerprint reader or allow the retina reader to render the tablet useable. In addition to the fingerprint and retina reader, other types of techniques, such as, but not limited to, voice recognition systems can also be employed without departing from the broader aspects of the present invention. Any of these "readers" can also be used in conjunction with other security protocols such as passwords or keys.

These types of readers can have particular utility in emergency situations where a patient may be able to speak but not move adequately to sign a release form. The patient can provide verbal permission which may be recorded by the tablet or other means and then the patient's fingerprint or retina can be scanned thereby granting access to the needed medical information. Where a patient is unconscious, a spouse, next of kin, or other person having power of attorney, can grant permission and the patient's fingerprint or retina can then be scanned. In all cases, the patient controls access to his/her clinical records, with there being an exception for care providers being able to access their own treatment records. In addition, a patient's photograph can be input into the database to provide for identity verification.

An additional security measure will be implemented whereby records once entered cannot be changed, even by the care provider that entered the records. All that will be allowed is that a care provider may input additional information to a record to amend the original record.

In order for anyone to enter information into the databases containing patient's records, they must be an approved member of a care provider network and he/she can enter only into his/her own record. To become a member of a network a fee may be assessed. A nominal fee may also be assessed to patients desiring to have their records maintained on the database. Once a member of the network, different access privileges may apply. For example, an insurance provider may only have access privileges to information pertaining to the information required to process an insurance claim. Pharmacies may only be granted access to information pertaining to patient medication. Where a pharmacy is a member of the network and care providers transmit prescription information to the pharmacy electronically, the pharmacy may also need to be equipped with security measures such as the fingerprint or retina reader.

Where a care provider is not in the above-described network but the patient wants his/her medical information pertaining to the treatment by the out-of-network care provider input into the database, the care provider can submit the information via fax, e-mail or other means to an entity authorized to enter the information into the database on the patient's behalf. The same is true for in-network care providers who may not have internet access or otherwise be unable to input information directly into the database.

In addition to the patient's records being accessible via a programmed tablet or server and the database, a patient can also be provided with a smart card or memory stick or even a CD having their clinical records thereon. The card could then be swiped through a card reader either at the facility where the patient is present, or the card reader can form part of a care provider's tablet. The card can be programmed with all or part of a patient's clinical records. These records can be added to by different care providers in the network into their respective clinical records for the particular patient by downloading the information onto the card during a patient's visit. The same holds true for a memory stick or CD.

BRIEF DESCRIPTION OF THE DRAWINGS

FIG. 1 is a flow chart illustrating a method of the present invention for assuring secure access to patients' clinical records.

FIG. 2 and FIG. 2A together comprise a chart illustrating the major components of a wireless data entry devise for patient clinical records.

FIG. 3 and FIG. 3A together comprise a flow chart illustrating a method of tracking patient and patients' clinical records.

DETAILED DESCRIPTION OF THE PREFERRED EMBODIMENTS

Figure 3:
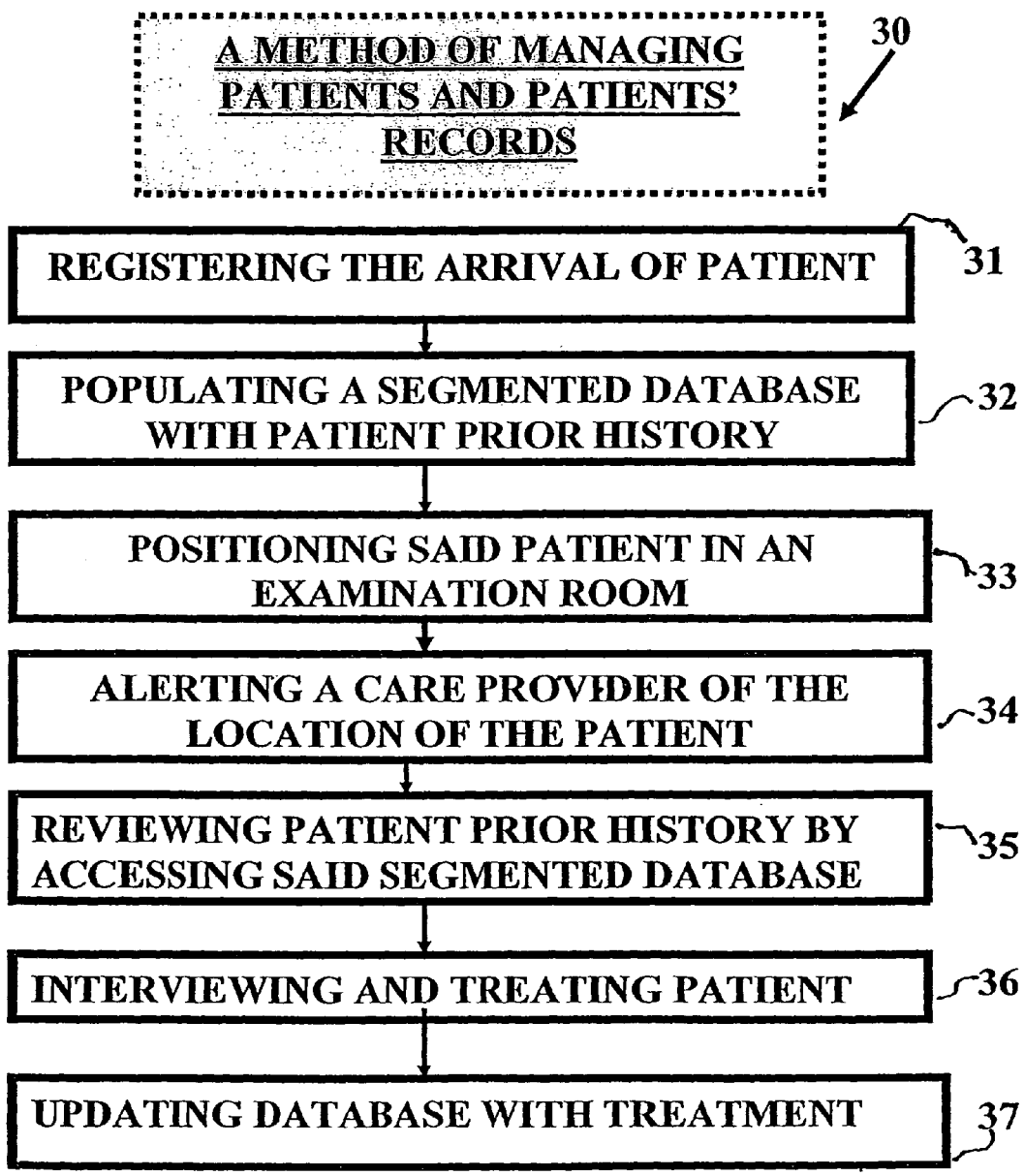

As used herein, the term "care provider" should be broadly construed to include, but not be limited to, doctors, nurses, physician's assistants, emergency medical technicians, paramedics, nursing home workers, pharmacists, diagnostic laboratories and medical testing facilities authorized to access the clinical records.

FIG. 1 illustrates a method for secure access to patients' clinical records 10; a database 12 is established for containing patient clinical records. This database can be internal to a practice or facility or it can be accessible via the internet or other secure server by any number of care providers authorized by the patient to access the clinical records. Medical information 14 is input into the database by authorized care providers or staff. The database 12 is segmented or divided into different areas. A particular care provides may have access to different areas in the database, however, the care provider can only input data or other information into the area associated with the particular care provider's practice. A care provider will not be allowed to change any information contained within the database. However, the care provider may annotate (not change) information that he/she has previously input into the database. In all cases, protocols for access permissions 16 are provided. While a care provider may have access to the database to input information regarding his/her care of the patient, the provider may not input into other provider's records. With the patient's approval access to the database is authorized 18; a care provider may view other care provider's records but cannot make any input into other care provider's records of the patient.

As shown in FIGS. 2 and 2A portable data or communications devices 20 derived partially from current devices such as personal digital assistants, pocket personal computers, laptop computers and tablet-based devices that include touch screen technology are used in the present invention and are collectively referred to as "tablets." Preferably, these tablets are equipped with various features, such as, but not limited to wireless technology 22 to allow the tablet to access and receive information as well as input and upload information to the database without having to be directly connected via a hard wire to a server, modem, DSL line or other hard wired connection. The tablet 20 includes a visual data display 24 typically a visual display screen of any suitable type, wireless data transmission hardware and software 22; data input device 26 such as a keyboard 26a, touch screen 26b which may include a writing screen surface to allow for handwritten notes to be input, voice/audio input 26c with optional voice recognition capability; and functionality (internally stored or via wireless to a central server). FIG. 2A sets forth optionally desirable functionalities of the device 20 including access to calendaring for scheduling 21, accepting messages 23, local CPU and data storage 25, software for display multiple patient records from multiple databases 27, real-time communication with a central server 29 which can have all the capabilities shown in 29a and 29b. While the tablet 20 has been described as incorporating a plurality of different features, the present invention is not limited in this regard as more or few features can be incorporated into the tablet without departing from the broader aspects of the present invention.

Referring now to FIG. 3, the method of managing patients and patients' records 30 is generally illustrated as a flowchart. The care provider can access a calendaring function that provides a list of all of his/her appointments for a desired time period on his/her tablet. This list of appointments can be loaded into the tablet 20 at one or more daily intervals or the list of appointments can be remotely updated by support staff or other personnel at the care provider's facility via a computer or another tablet. This update can occur whenever a care provider's tablet is connected to the internet or to an intranet, or the update function can occur wirelessly by known methods. When a patient enters and registers 31 at the facility for treatment and, if the individual is a first-time patient or an update of the medical history is necessary, is given a medical history form to fill out. This step of populating a segmented patient records database with patient history 32 can take several forms. If the patient is computer literate, the patient can be provided with a tablet to input the required information or, if the database is accessible over the Internet, prior to his/her appointment, the patient can input the required information from their home or office computer. The computerized form will be set up and segmented to be easily understood and user friendly to manipulate. If the patient is not computer literate, a staff member can input the information based on a paper form filled out by the patient. In either situation, the information, or portions thereof, provided by the patient is ultimately uploaded to, and stored in the database.

Still referring to FIG. 3, once the patient information is input into the database, the patient is generally escorted or sent to an examination room 33. The examination room into which the patient has been sent is input into the database or into a program that, among other things, provides access to, and allows for data manipulation regarding the information contained within the database. Once the patient is in the examination room, the care provider is alerted 34 via an indicator on his/her tablet. The indicator can be audible, visual (a flashing portion of the screen or a blinking light), or a combination of visual and audible signals. In addition, the alert can take the form of a pop-up window or screen on the tablet's display. Such a signal can provide all if the information concerning the patient's identity and location, or the alert can be clickable and lead to a screen containing the desired information. Once alerted, the care provider can then tap or "click" an icon on the screen of his/her tablet corresponding to the examination room in which the patient has been placed and the patient's name and the information corresponding to the patient's last encounter appear on the tablet screen. The care provider is able to scroll to previous encounter information or search history by date and type of each segmented file 35.

As the patient's examination 36 progresses, the care provider will input information 37 via the tablet. This can be accomplished by either typing the information into the tablet or by writing on the surface of the tablet that is programmed with character recognition software to convert the handwritten notations into the equivalent of typed text. Where the information is handwritten, a copy of the actual handwritten notes along with a copy of the converted typed notes can be saved so that if errors in the converted notes occur, the handwritten notes can be referred to. In addition, when inputting information, the program can allow the care provider to access a list of common phrases or diagnoses or other templates that the care provider may wish to input. In addition, the tablets can include, or be provided with, a microphone and be programmed with voice recognition software. In this case, a care provider can dictate into the tablet which automatically converts the dictation into transcribed text. The transcribed text as well as the recording of the dictation is then stored in the database.

Returning to the above-described example as illustrated in FIG. 3A, if during a patient visit, the care provider orders tests 38 to be conducted on a patient, the care provider can attend to other patients in the above-described manner while the first patient is undergoing the tests 39. Once the tests are completed 40, the facility or entity conducting these tests accesses the database and inputs the test results 41. Upon return after having had the prescribed tests, the patient is placed in the same or a different examination room. The care provider is alerted via his/her tablet as described above and clicks or taps on the icon displayed on the tablet corresponding to the examination room that the patient is in and is once again presented with information corresponding to the particular patient in the chosen examination room. The care provider can access the test results 42, analyze them 43 and discuss them with the patient 44. Where a period of time is required to obtain the test results, the tablet can also be used to alert the care provider that the results have been input into the database. The care provider can then contact the patient 44 via conventional methods, or he/she can use the tablet to e-mail, fax or call (if the tablet is so configured) the patient regarding the results of the test. Still referring to FIG. 3A, upon completion of a patient's visit to a care provider's facility, the care provider can input, using the tablet, the results of the visit and the patient's treatment plan 45. The care provider will input any necessary prescriptions 47, schedule a follow up visit 46 with automatic reminders 48 into the tablet. Reviewing the test results generally involves viewing X-rays, MRI, or CAT scan images. In the present invention, the tablet 20 can be programmed to allow the care provider to make annotations onto the image and to store the annotated images in the database.

Figure 4:
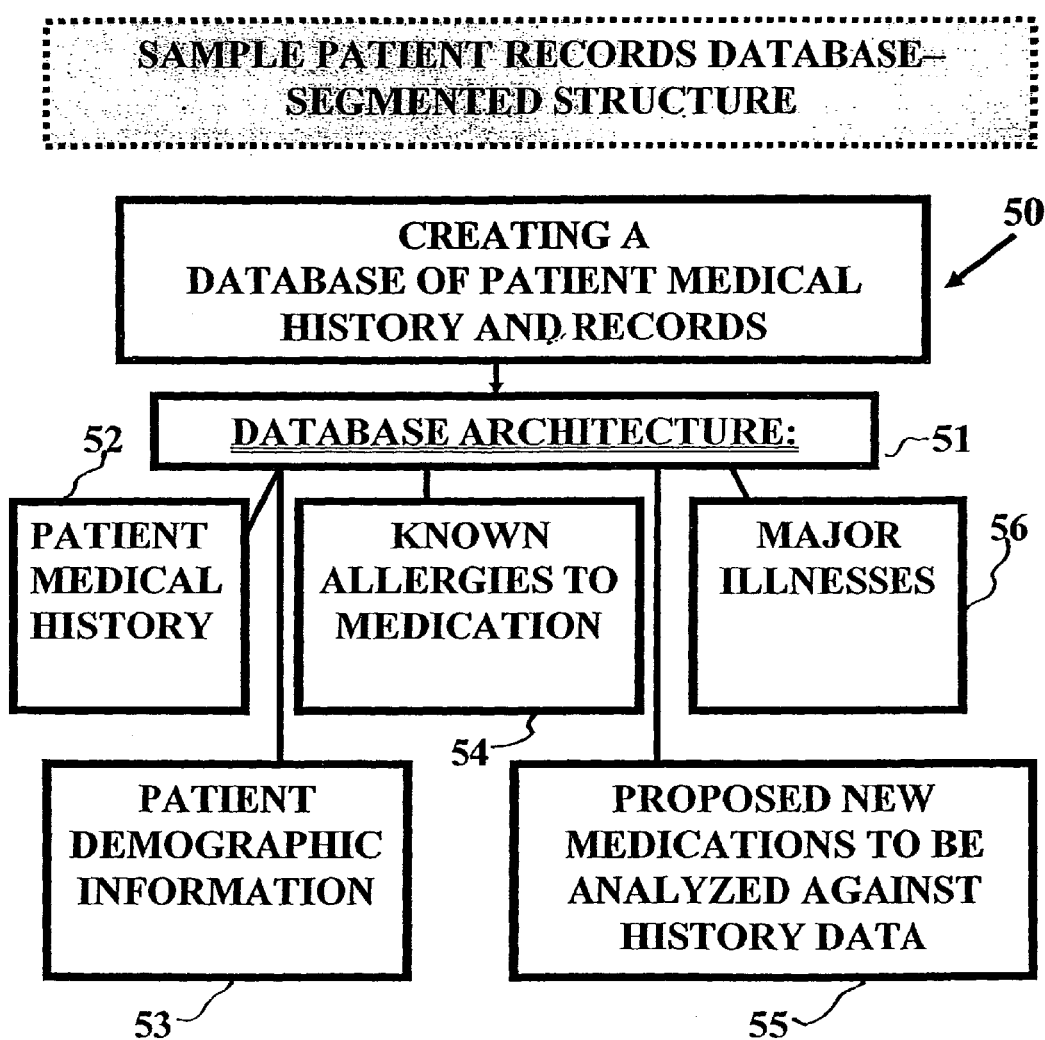
FIG. 4 is a chart illustrating a database architecture for patient clinical records.

Referring back to the patient's medical history input 32 described in FIG. 3, it is helpful to expand the description of that history. FIG. 4 illustrates the character of a sample patient records database 50 with a segmented structure, also called database architecture 51. Electronic filing cabinets are used as typical graphical screen display of such architecture. At a minimum, the information required from a patient will include patient's medical history 52, demographic information 53, known allergies to medications 54, current medications being taken 55 and major illnesses 56. This information will be stored in the database in a segmented format with allergies to medications as one segment, current medications being taken forming another segment or category, major illnesses being another category, etc. The medical/clinical information can be input into the database by the care provider or other personnel. In addition, and providing the proper access privileges are complied with, the information can be put into the database by the patient.

In the graphical display of the data from the database, information can conveniently appear in the form of a series of drop-down menus or "electronic filing cabinets" corresponding to various segmented aspects of the patient's medical history, or the complete history of the patient can be displayed with the care provider being able to scroll down the history or to search using keywords or dates. When a care provider wishes to input notations concerning a patient, he/she would preferably open an electronic filing cabinet by "tapping" or "clicking" an icon on the tablet screen corresponding to the desired filing cabinet. Once open, the doctor can search the contents of the particular electronic filing cabinet by keywords, date, or by scrolling. If the care provider wishes to add material to the contents of the electronic filing cabinet, the care provider can start typing or writing on a touch-screen and the program will automatically input the information following the last entry.

Figure 5:
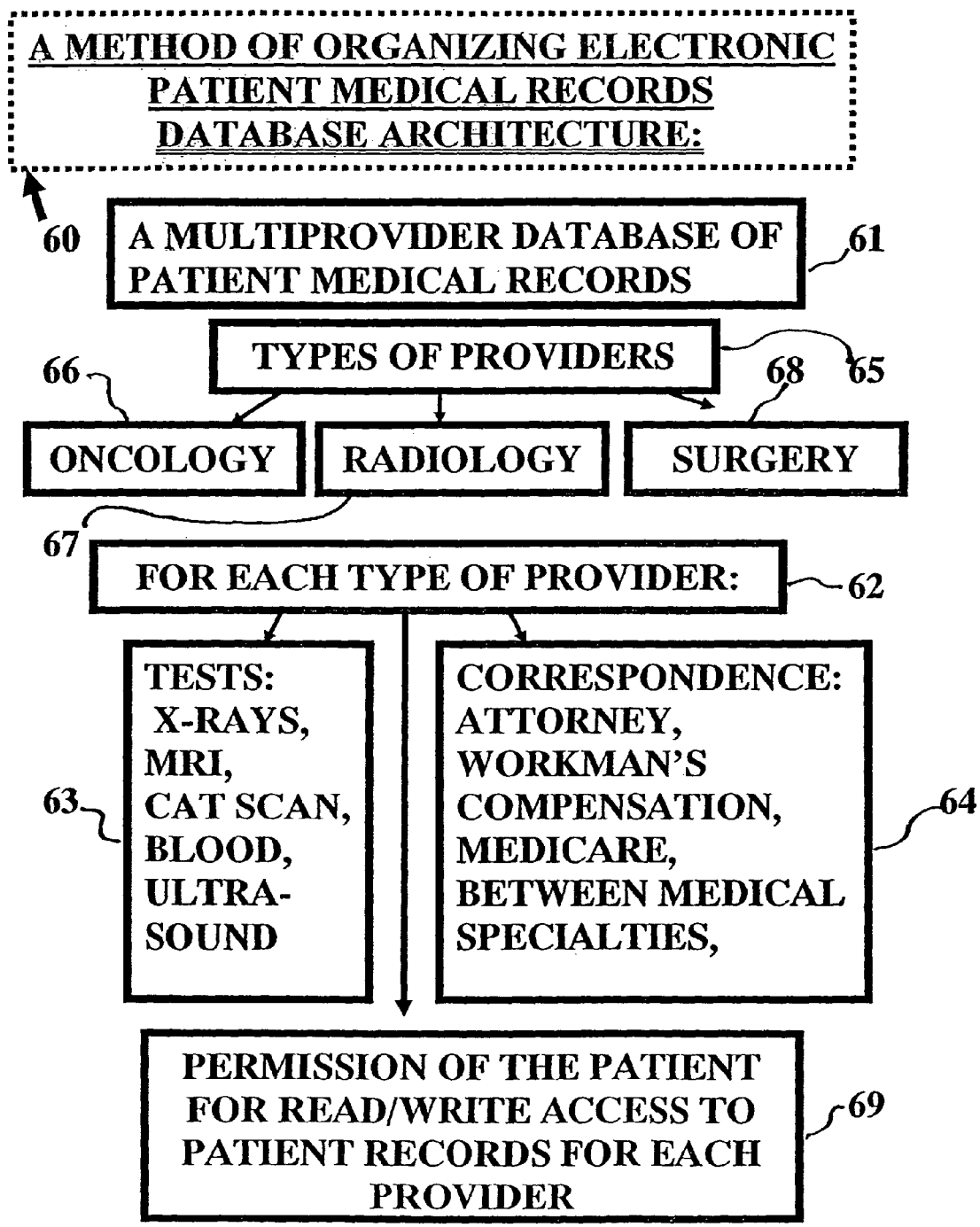
FIG. 5 is a flow chart illustrating a method of organizing electronic patient clinical records.

FIG. 5 illustrates a preferred method of organizing electronic patient clinical records 60 with database architecture involving a multiprovider database 61. Each care provider 62 can have access to a number of different electronic filing cabinets. For example, there can be filing cabinets for tests 63 such as pathology, X-rays, MRI's, CAT scans, blood tests and ultrasounds. Filing cabinets can contain many types of correspondence 64 such as attorney's correspondence, Medicare, workman's compensation, and correspondence between doctors. However, these lists should not be considered exhaustive as any number of different filing cabinets can be set up and accessed. The information can also be scanned in or be electronically entered.

In addition, there will be electronic filing cabinets established for different medical specialties 65. A few such specialties may be oncology 66, radiology 67 and surgery 68. When a specialty is accessed, the software provides a visual display of a list of doctors or other care providers of the patient that will appear on the tablet and be selectable by the care provider accessing the electronic filing cabinet, with the patient's permission 69. Within each specialty, once a particular care provider is chosen, the current provider can access and view that record but not amend or add to the record. A provider can only add or amend his/her own record for the patient.

Figure 6:
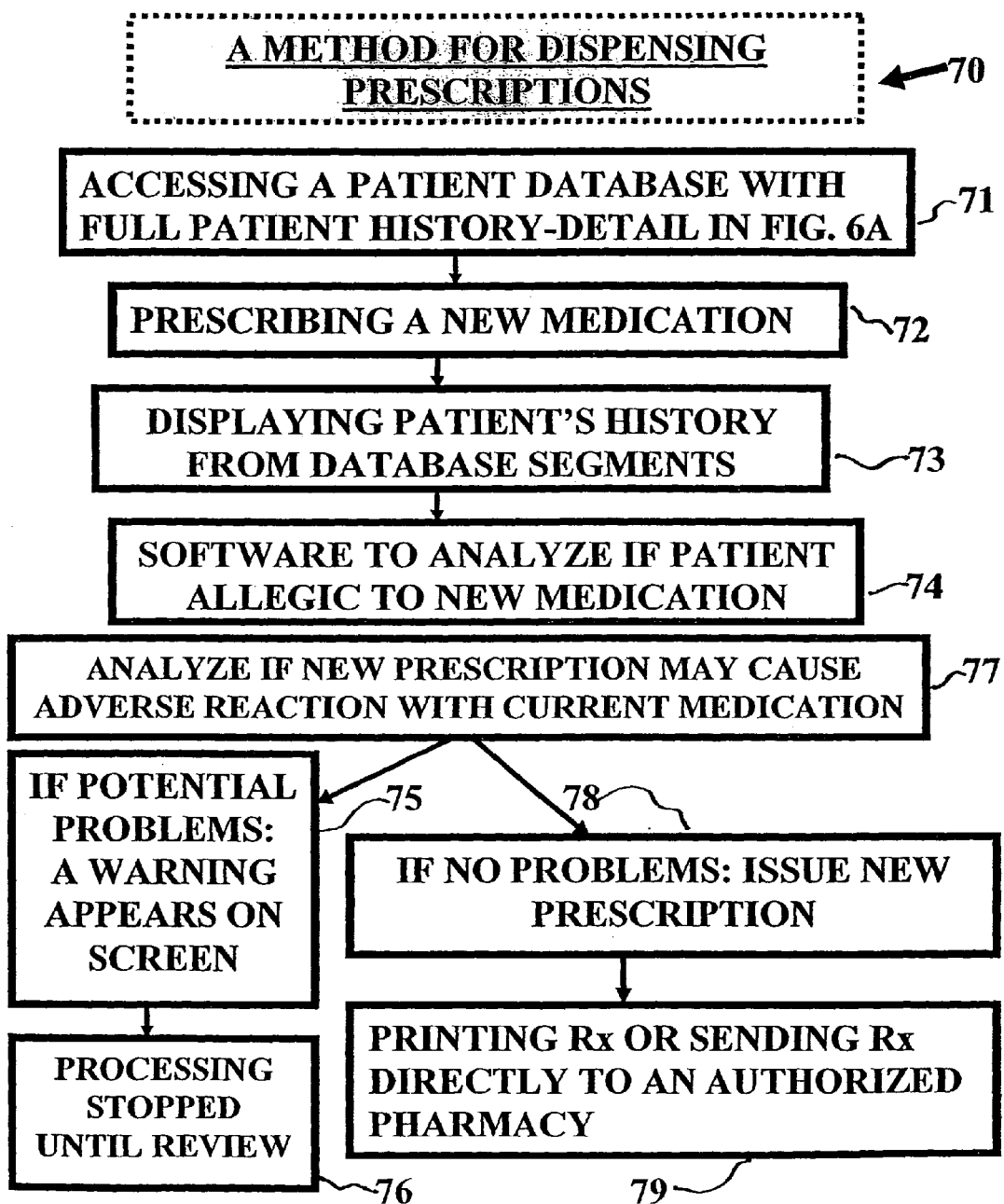
FIG. 6 is a flow chart illustrating a method for dispensing prescriptions.

FIG. 6 sets out a method for dispensing prescriptions 70 preferably utilizing the hand-held tablets with their real time communication capabilities. When a care provider accesses 71 the electronic filing cabinet corresponding to writing the prescriptions 72, the particular patient's drug allergy and other patient medical history relating to medication information is also displayed 73. If a care provider attempts to prescribe a drug to which the patient is allergic, the software will detect the allergic potential 74 and the tablet will alert 75 the care provider and/or suspend further processing and prevent the prescription from being printed 76. In addition, the program running on the tablet will cross-reference the prescribed medication with any medications currently being taken by the patient and will compare the combination of drugs with reference sources, such as, but not limited to, the Physicians Desk Reference for any possible problems that may arise due to the medicinal combination 77. If no problems are detected, the prescription can be printed either remotely at a staff person's work station, at a printer in the particular examination room 78, or if the tablet is so equipped, via an integral printer forming part of the tablet. The prescription can also be faxed or e-mailed to an authorized pharmacy 79 directly from the tablet.

If at any time a care provider needs to convey information to another care provider or staff member, the tablet can be programmed to call the other person(s) on their cell phone and a message can be played upon answer. In addition, the tablet can send an instant message to the cell phone or can page the person(s) via their beeper. The tablet can also be configured to accept messages from other tablets, cell phones, beepers, and other communications devices. Moreover, the tablet can be configured to cause a message to be printed at a desired location, such as, for example, in a hospital a doctor can use his/her tablet to order a test and while the patient is going to the area where the test is to be performed, the physician's instructions can be printed there.

Figure 7:
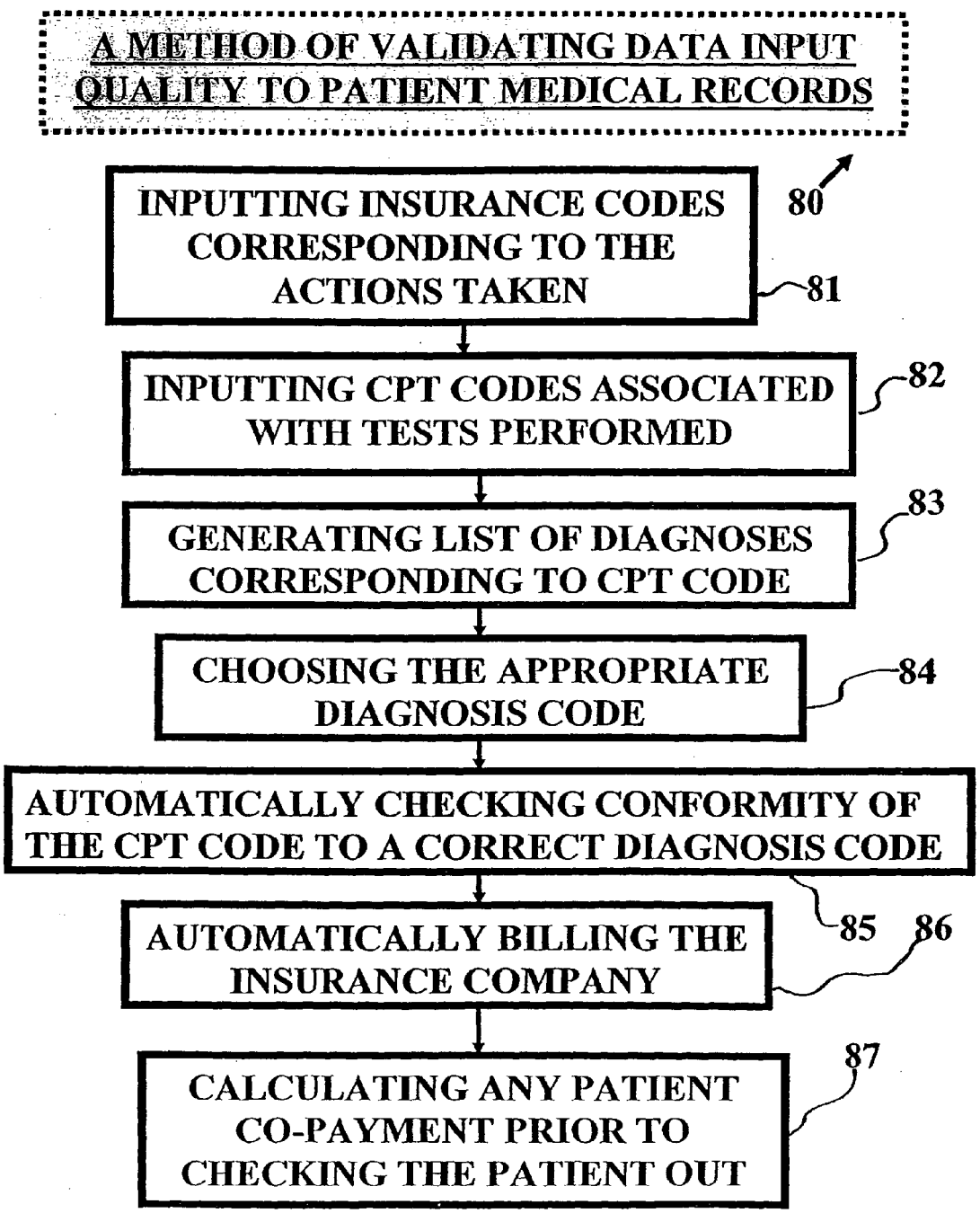
FIG. 7 is a flow chart illustrating a method of validating data input for patients' clinical records.

Accurate record keeping is an important part of the patient care process. What has been long needed is an improved method of validating data input quality to patient clinical records 80 shown in flowchart form on FIG. 7. Upon completion of the patient's visit, the care provider or a staff person will input insurance codes corresponding to the actions taken 81 with respect to the patient during the visit. The software program running on the tablet will interface with appropriate reference sources to insure that the proper insurance codes have been associated with the visit. This will minimize and perhaps prevent over-coding or under-coding with respect to the particular visit. When a care provider inputs a CPT code (CPT®—Current Procedural Terminology is a registered trademark of the American Medical Association) associated with tests performed 82 on the patient, a list of diagnoses corresponding to the particular CPT code 83 chosen can appear and then the care provider can choose the appropriate diagnosis code. The software checks for conformity of the choice made 85. Once the appropriate CPT code corresponding to the correct diagnosis code entry is complete 84, the insurance company can be automatically billed 86 and any patient co-payment can be indicated 87 prior to patient checking out of the facility.

Any follow-up visits to the care provider's facility can be input via a tablet with e-mail or fax reminders being automatically sent or standard mail reminders automatically generated. This information is also available to the secretary who is checking the patient out.

In another aspect of the present invention, when a patient has a question for a care provider, or has an emergency, the patient, a staff person, or an answering service can send a message via e-mail or telephone to the care provider's tablet. An indicator on the tablet will alert the care provider regarding the fact that there is a patient message. Depending on whether the message concerns an emergency or not, the alert level can change and may consist of flashing lights of differing colors, an audible alert, a message on a particular section of the tablet screen, or any combination thereof. Using the tablet, an authorized care provider can access a patient's medical history from any location where wireless or other access to the database is available. There will be a message queue indicating the order in which the messages were received. Depending on the decided upon manner of response, the care provider can e-mail the patient, call the patient, or e-mail instructions to a staff person to call the patient. The care provider can also use the tablet to send a fax to the patient.

Figure 8:
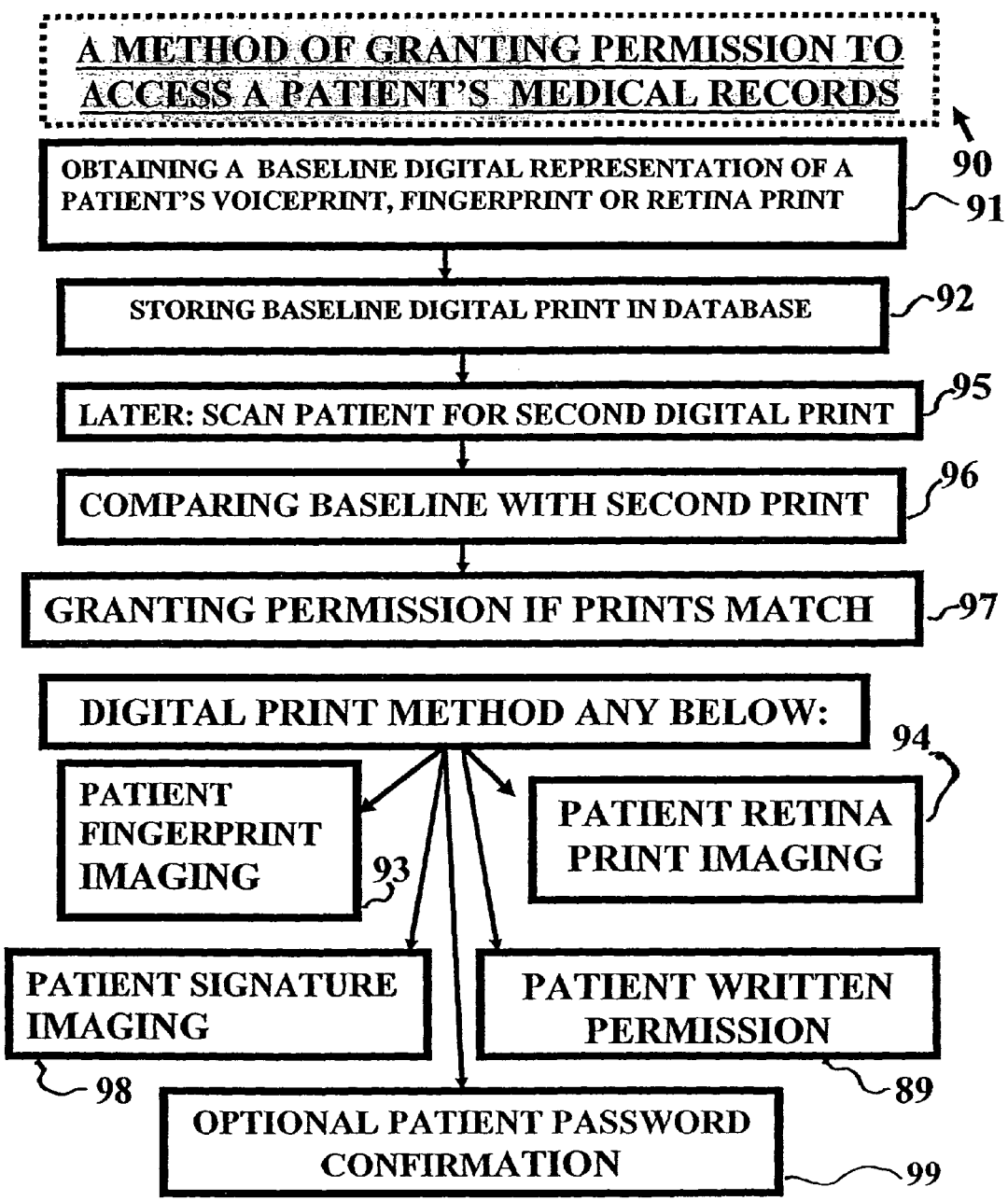
FIG. 8 is a flow chart illustrating a method of granting permission to access a patient's clinical records.

The above described embodiments of the present invention are all predicated on high levels of security with respect to anyone having access to a patient's clinical records. The present invention is completely HIPPA compliant. Absolutely no access to a patient's records of another care provider will be permitted without first obtaining a patient's permission. (A provider can always view his/her own record of the patient.) Such permission can be given in a conventional manner by providing the entity desiring access with written permission 89. Another aspect of the invention is shown in FIG. 8 where a flowchart shows the main elements of a method of granting permission to access a patient's clinical records 90 employing a fingerprint or retina print recognition system whereby a baseline digital representation 91 of a patient's thumbprint or other fingerprint or retina print is stored in the database 92 either separately or along with the particular patient's demographic information. A fingerprint or retina print reader can be located in a care provider's facility and when a patient arrives, his/her fingerprint 93 or retina print 94 can be scanned to create a second digital print 95 by the fingerprint or retina reader. The baseline print is compared to the second digital print 96 and in this manner permission to access the patient's clinical records is granted 97. The patient can also be required to enter a password 99 along with the fingerprint or retina print. Digital signature imaging 98 may also be employed similar to that used on credit card debiting machines currently. Once the security protocols have been met, a series of icons or other indicia can appear. The icons represent various different segmented files of the medical record as illustrated in FIG. 4 and FIG. 5. The patient can then choose the icons corresponding to the records that he/she wishes to give the care provider access to.

Figure 9:
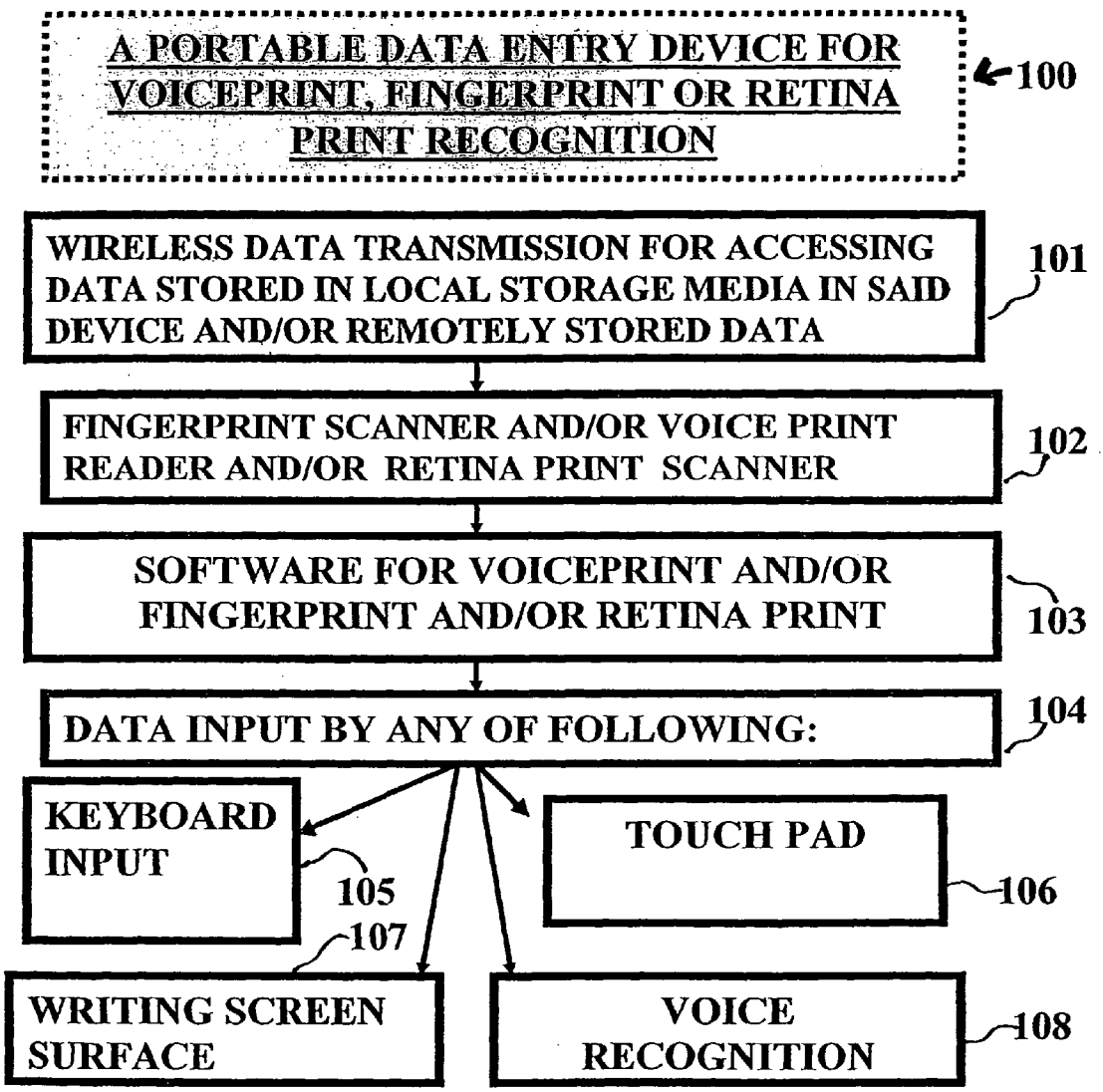
FIG. 9 is a chart illustrating the major components of a portable data entry device for voiceprints, fingerprints or retinal prints.

Referring now to FIG. 9, the above-described fingerprint or retina print reader can also be incorporated into the care provider's personal tablet. In this aspect of the invention, a portable data entry device for voiceprint, fingerprint or retina print recognition 100 includes wireless capabilities 101, a scanner for taking prints 102 and software for taking, interpreting and comparing the prints 103. The device has the data input capabilities 104 such as keyboard 105, touch pad 106, writing screen 107 voice input 108. These and other functionalities have already been described in conjunction with FIG. 2. The patient would then grant permission using the care-provider's tablet in the manner described in the foregoing paragraph.

Figure 10:
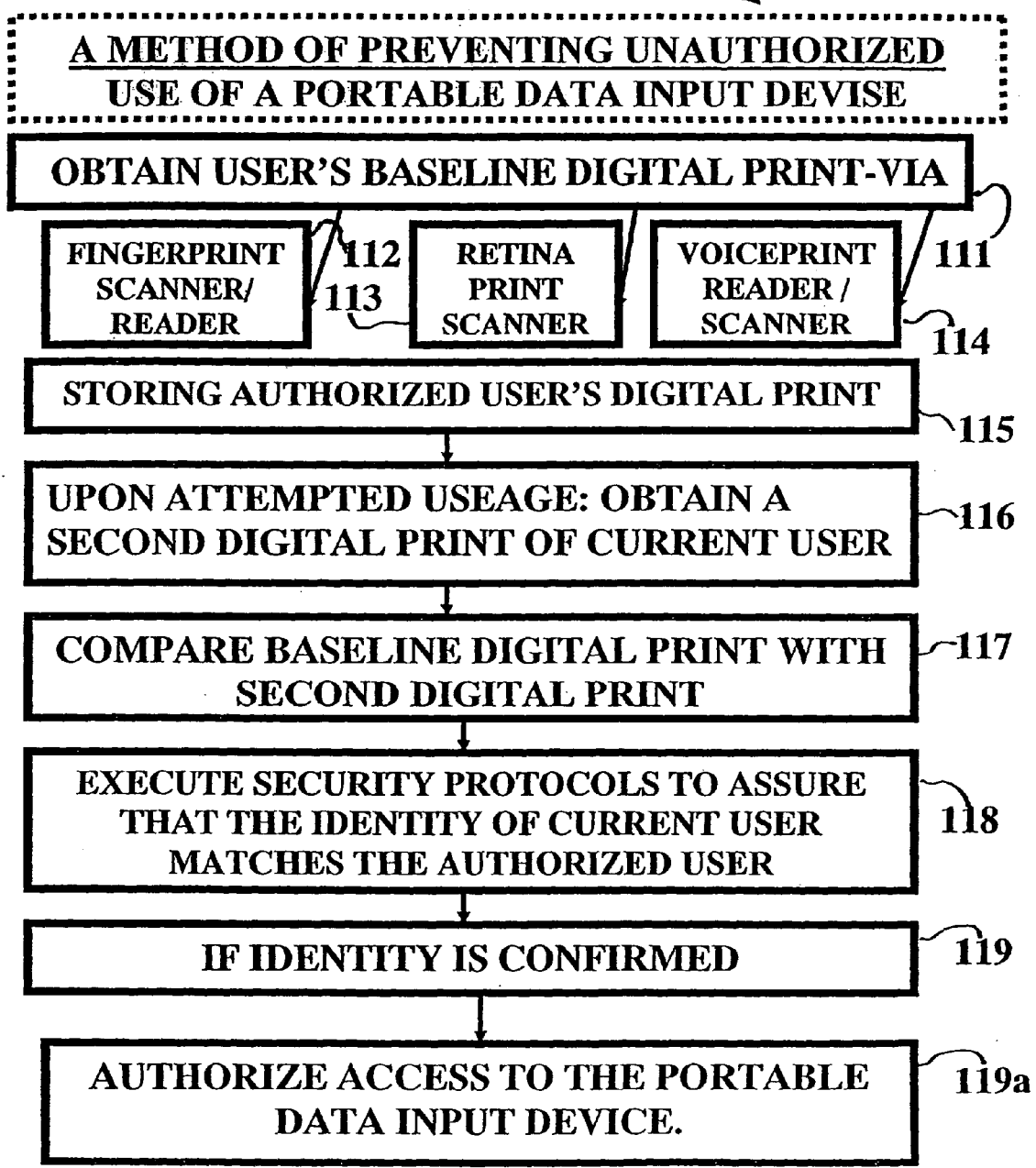
FIG. 10 is a flow chart illustrating method of preventing unauthorized use of a portable data input device.

In addition, as shown in FIG. 10, the fingerprint or retina print reader can also be employed to prevent unauthorized use of a particular tablet 110. An original baseline print for the authorized user is obtained 111 using fingerprint scanner 112 or retina print scanner 113 or voiceprint reader 114. It is stored 115 locally on the devise. When such is the case, the care provider would have to swipe his/her finger over the fingerprint reader or allow the retina reader to obtain a second print 116 to compare 117 to the baseline print 11. Upon affirmative execution of predetermined security protocols to assure that the identity of the new user is the same as the authorized user 118, such identity is confirmed 119 and access to the tablet is granted 120. In addition to the fingerprint and retina reader, other types of techniques, such as, but not limited to, voice recognition systems 114 can also be employed without departing from the broader aspects of the present invention. Any of these "readers" can also be used in conjunction with other security protocols such as passwords or keys.

Figure 11:
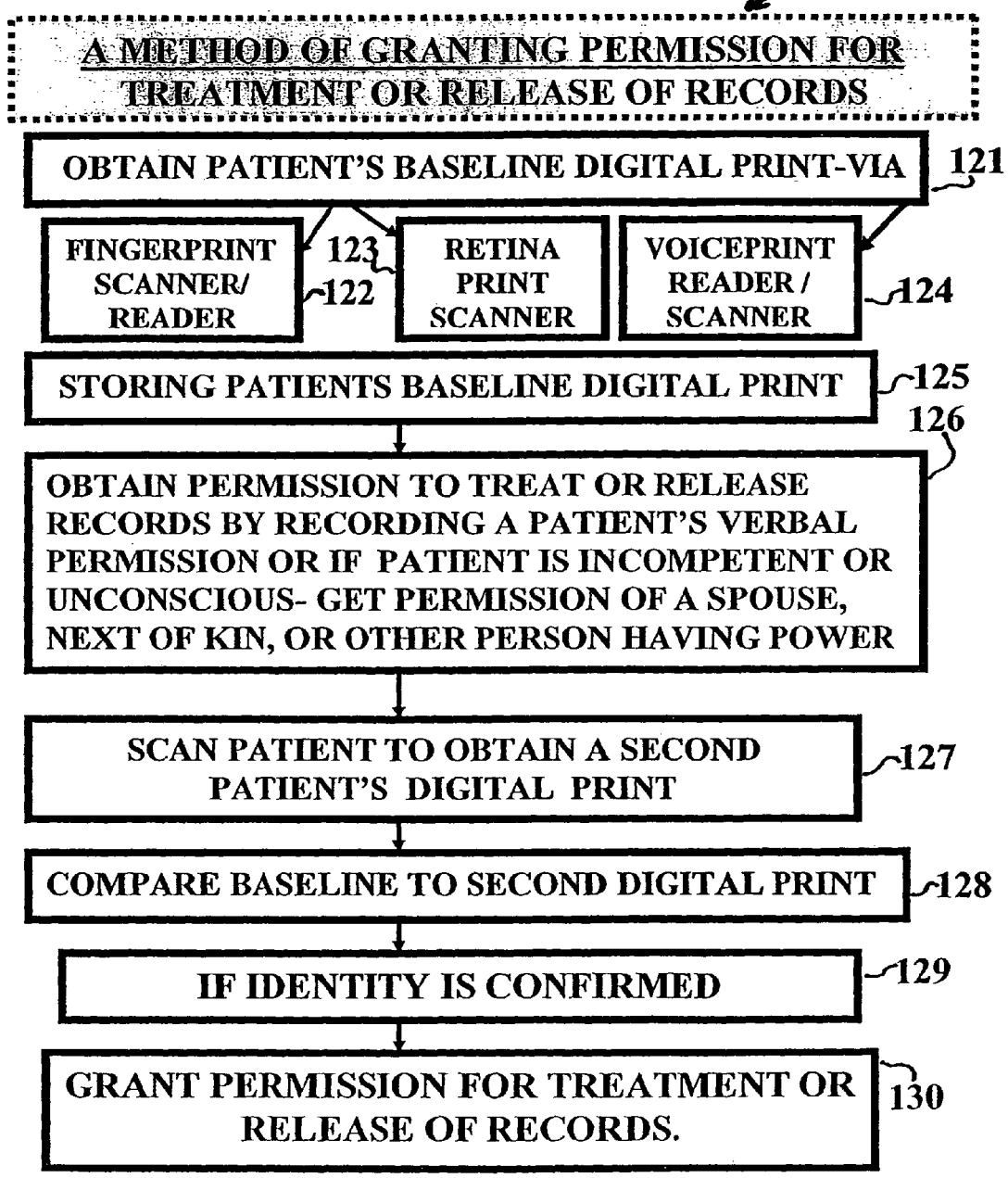
FIG. 11 is a flow chart illustrating a method of granting permission for medical treatment or release of clinical records.

These types of readers can have particular utility in emergency situations where a patient may be able to speak but not move adequately to sign a release form. FIG. 11 outlines the steps of the method of granting emergency permission to treat or release clinical records 120. Before the emergency arises, the patient's print is obtained 121 via fingerprint 122, retinal print 123 or voiceprint 124 and stored in a database 125. The patient can provide verbal permission, which may be recorded by the tablet or other means 126, and then the patient's fingerprint or retina can be scanned 127, thereby granting access to the needed medical information. Where a patient is unconscious, a spouse, next of kin, or other person having power of attorney, can grant permission and the patient's fingerprint or retina can then be scanned 126. The second print is compared to the baseline print 128 and if identity is confirmed 129, permission to treat or release records is granted 130. In addition, a patient's photograph can be input into the database to provide for additional identity verification.

In all cases, the patient controls access to his/her clinical records, with an exception that care providers can access their own treatment records. An additional security measure can be implemented whereby even the care provider that entered the records cannot change records once entered. All that will be allowed is that a care provider may input additional information to a record to amend the original record.

Figure 12:
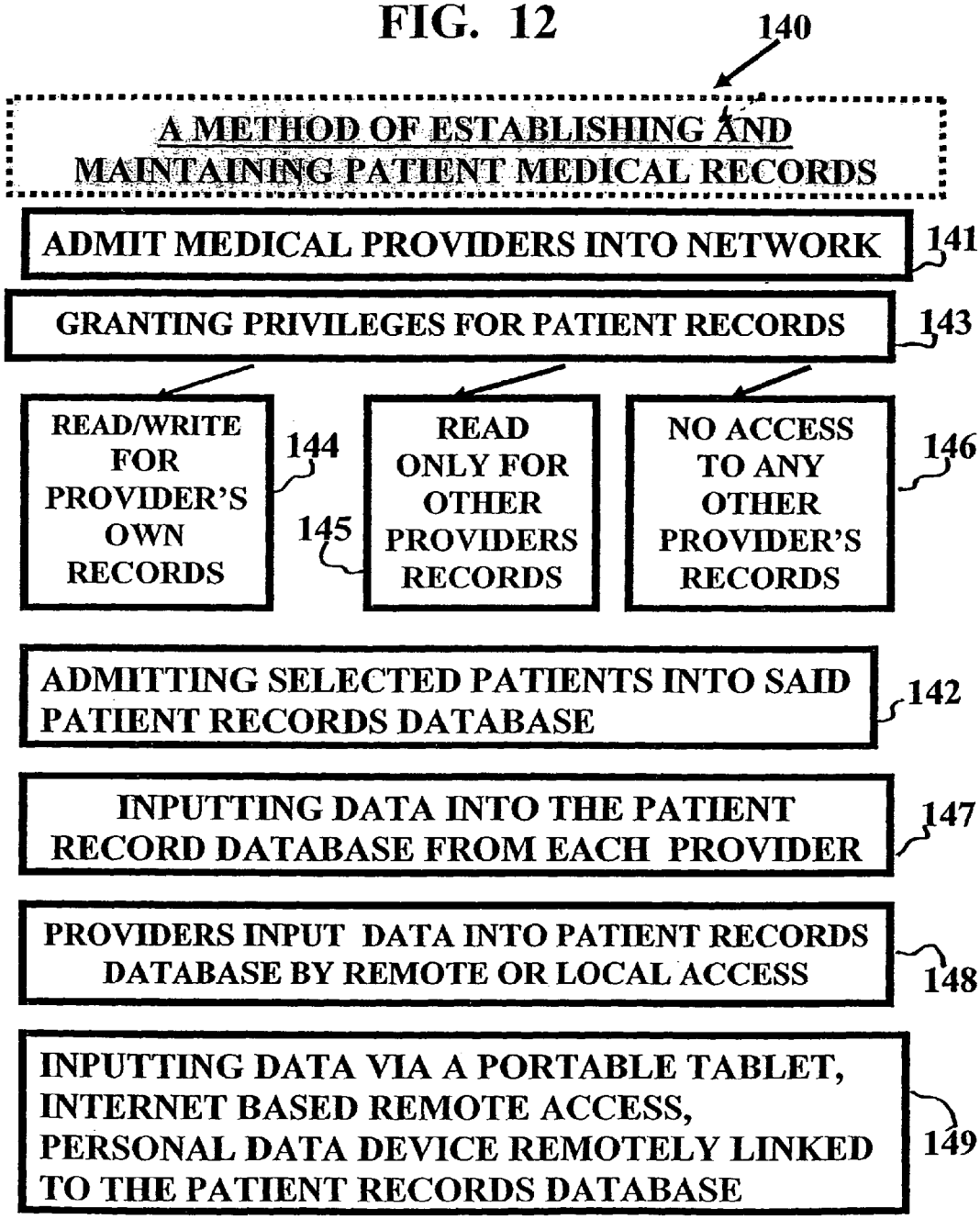
FIG. 12 is a flow chart illustrating a method of establishing and maintaining patient clinical records.

Still another aspect is shown in FIG. 12 where a large scale network of health care providers combine to offer to patient subscribers a centralized repository for all aspects of the patient's health care records. The method of establishing and maintaining patient records 140 begins with the method of providing security for patient records. In order for anyone to enter information into the databases containing patient's records, that person must be an approved member of a care provider network 141 and he/she can enter only into his/her own record. To become a member of a network a fee may be assessed. A nominal fee may also be assessed to patients desiring to have their records maintained on the database 142. Once a member of the network, different access privileges may apply. The following discussion presumes that the patient has approved 143 for the particular provider the level of access being discussed. A provider will have both read and write privileges 144 for that provider's own records. A provider will have read-only rights 145 to other relevant provider's records. A provider may have no rights to access to records of other providers 146 if patient has not approved such access. For example, an insurance provider may only have access privileges to information pertaining to the information required to process an insurance claim. Pharmacies may only be granted access to information pertaining to patient medication. Where a pharmacy is a member of the network and care providers transmit prescription information to the pharmacy electronically, the pharmacy may also need to be equipped with security measures such as the fingerprint or retina reader.

Once the provider is in the network, they may input data 148 by remote access or provide it locally to the network administrators to enter on their behalf. As the provider gives current care to the patient, the new data can be entered via Internet, portable tablet or other portable devises 149 previously described above. Where a care provider is not in the above-described network but the patient wants his/her medical information pertaining to the treatment by the out-of-network care provider inputted into the database 147, the care provider can submit the information via fax, e-mail or other means to an entity authorized to enter the information into the database on the patient's behalf. The same is true for in-network care providers who may not have Internet access or otherwise be unable to input information directly into the database.

In addition to the patient's records being accessible via a programmed tablet or via other remote access to the server and the patient records database, a patient can also be provided with a smart card or memory stick or even a CD having their clinical records thereon. The card could then be swiped through a card reader either at the facility where the patient is present, or the card reader can form part of a care provider's tablet. The card can be programmed with all or part of a patient's clinical records. These records can be added to by different care providers in the network inputting new data into their respective clinical records for the particular patient by downloading the information onto the card during a patient's visit. The same holds true for a memory stick, CD, DVD or any other removable data medium that usable with computer systems.

The present invention also resides in allowing pharmaceutical or other companies to advertise their products and/or medications. In the case of advertising for medications, when a care provider seeks access to a patient's medical records or otherwise accesses the software-based programming associated with the database where medical records are stored, the medication advertisement will be displayed to the health care provider or other user accessing the software. In the preferred embodiment, the health care provider or user can be given the option of ignoring the software by clicking an icon on the display or using a keystroke or keystroke combination. If the user decides to learn more about the advertised product, the user can, via keystroke or by clicking an icon on the screen, be sent to a web page that gives further information on the advertised medication. This further information can include such things as information pertaining to what the medication is used to treat, dosages, side effects and other contra-indications. The user can also have the option of accessing a summary of the information pertaining to the medication. This summary can be in bullet point or other outline-type format. However, the present invention is not limited in this regard as the summary could simply be in written paragraph form also.

The user can study the above-described summary information. Once the summary information is presented to the user, the user can have the option of accessing an on-line test that examines the user's knowledge of the advertised medication. The user can opt to take the test or to skip it. If the user takes the test, a score pertaining to the questions on the test answered correctly, will be given to the user. This score can be displayed immediately after taking the test, if all of the questions are in multiple choice or true/false format. However, the present invention is not limited in this regard as the user can also be e-mailed the test score or be required to check on-line at a particular webpage subsequent to taking the test. If essay-type answers are required to be typed in, the user may be required to check a webpage for the score or the score can be e-mailed to the user.

The above-described tests can be employed to give Continuing Medical Education (CME) credit for taking and passing them. The number of times a test can be taken and the amount of credit given will be governed by the appropriate CME authority.

The above-described test can also be triggered by a healthcare provider using the software to write a prescription for a given drug. Once the prescription is electronically written, the above-described summary will be displayed and the above-described test can then be taken. Taking and passing the tests can also provide a basis for the health care provider to be payed for performance by the relevant insurance company or other agency.

The present invention also resides in a series of icons that are displayed to the health care provider or user of the software associated with the database. These icons are positioned on the displayed device of the user and appear in certain areas of pages where such icons would be appropriate. For example, when a health care provider is viewing progress notes on the display an icon can also be visible that allows a screen pertaining to prescriptions to be called up when clicked. On this screen an icon can appear that provides for a review of the medicines a patient is currently taking, allergies to medications and any major illnesses the patient has or has had.

The software described above can also provide for the use of an icon to take a user to an area or screen that facilitates insurance coding for the services rendered to a patient on a particular visit. When this icon is selected the user is taken to a page where the healthcare provider describes by selecting different options, what was done for the patient. Evaluation and management codes will be suggested that are appropriate to a particular locale and/or for a particular insurance company. The information presented to a health care provider for selection is customizable to suit a particular practice and/or insure company's requirements.

In addition to the foregoing, forms typically used by healthcare providers can also be stored in the database and selectable therefrom. These forms may be sorted by specialty or by individual health care providers. In addition, the forms can be customized by a particular health care provider. In addition, homecare instructions can also be stored in the database and selected by the healthcare provider. These instructions can be customized by the healthcare provider and printed, faxed, or e-mail to the appropriate person(s).

Preventive health literature as well as test requisition forms can also be stored in and selectable from the database. These documents can also be customizable and printed, faxed or e-mailed to the appropriate person(s).

What is claimed is:

1. A method comprising:
   transmitting, via a portable tablet, a request to receive at least a portion of medical records of a patient;
   receiving, at the portable tablet, the medical records and a summary associated with a medication;
   entering, by a care provider on the portable tablet, a prescription for the medication;
   in response to entering the prescription for the medication via the portable tablet, presenting, on the portable tablet, a test that examines knowledge of the care provider concerning the medication, including information pertaining to what the medication is used to treat, dosages, side effects and other contra-indications, wherein the test is based on the information pertaining to the medication; and
   entering, by the care provider on the portable tablet, answers to the test;
   scoring the test as a pass or fail; and
   paying for services rendered to the patient by the care provider, based on the care provider passing the test.

2. The method of claim 1, further comprising:
   receiving, at the portable tablet, an advertisement associated with the medication.

3. The method of claim 1, wherein transmitting the request to receive the medical records comprises:
   transmitting a request by selecting one of a plurality of selectable icons from a plurality of icons associated with segments of the medical records.

4. The method of claim 3, wherein receiving the at least portion of the medical records and the summary associated with the medication comprises:
   receiving a segment of the medical records associated with the transmitted request.

5. The method of claim 1, further comprising:
   presenting an option to receive further information about the medication; and receiving, at the portable tablet, the further information associated with the medication.

6. The method of claim 1, wherein the medication is one of one or more mediations that the patient is currently taking.

7. The method of claim 1, wherein the medication has been recommended for treating an illness within the medical records.

* * * * *